(12) United States Patent
Ecker et al.

(10) Patent No.: US 9,605,260 B2
(45) Date of Patent: Mar. 28, 2017

(54) ALTERATION OF NEURONAL GENE EXPRESSION BY SYNTHETIC PIRNAS AND BY ALTERATION OF PIRNA FUNCTION

(71) Applicant: IBIS BIOSCIENCES, INC., Carlsbad, CA (US)

(72) Inventors: David J. Ecker, Encinitas, CA (US); Todd P. Michael, Carlsbad, CA (US); Lendell L. Cummins, San Diego, CA (US); Mark W. Eshoo, San Diego, CA (US); Stanley T. Motley, Carlsbad, CA (US); Danny M. Chou, Carlsbad, CA (US)

(73) Assignee: IBIS BIOSCIENCES, INC., Carlsbad, CA (US)

( * ) Notice: Subject to any disclaimer, the term of this patent is extended or adjusted under 35 U.S.C. 154(b) by 0 days.

(21) Appl. No.: 14/212,412

(22) Filed: Mar. 14, 2014

(65) Prior Publication Data

US 2014/0275216 A1 Sep. 18, 2014

Related U.S. Application Data

(60) Provisional application No. 61/784,353, filed on Mar. 14, 2013.

(51) Int. Cl.
*C12N 15/113* (2010.01)
*C12Q 1/68* (2006.01)

(52) U.S. Cl.
CPC .......... *C12N 15/113* (2013.01); *C12Q 1/6883* (2013.01); *C12N 2310/10* (2013.01); *C12N 2320/11* (2013.01); *C12Q 2600/154* (2013.01)

(58) Field of Classification Search
USPC ......... 435/6.11, 6.13, 6.16, 91.1, 287.2, 375, 435/377, 6.1, 91.31, 455; 514/44, 17.7, 1, 514/2; 536/23.1, 24.3, 24.5; 424/9.1
See application file for complete search history.

(56) References Cited

U.S. PATENT DOCUMENTS

| | | | |
|---|---|---|---|
| 6,945,969 B1 * | 9/2005 | Morris et al. | 604/508 |
| 2002/0054902 A1 | 5/2002 | Pardridge | |
| 2006/0141600 A1 | 6/2006 | Joshua-Tor et al. | |
| 2009/0062228 A1 | 3/2009 | Hannon et al. | |

OTHER PUBLICATIONS

Rajasethupathy et al, Cell, vol. 149, pp. 693-707 (Apr. 27, 2012).*
Day et al, Nature Neuroscience, vol. 13, No. 11, pp. 1319-1323 (2010).*
Lee et al, RNA, vol. 17, pp. 1090-1099 (2011).*
Miller et al (Nature Neuroscience, vol. 13, No. 6, pp. 664-666 (2010).*
Miller et al, Neuron, vol. 53, pp. 857-869 (2007).*
Lister et al (Nature, vol. 462, No. 7271, pp. 315-322 (2009).*
Aravin A. A., et al., "A piRNA Pathway Primed by Individual Transposons is Linked to De Novo DNA Methylation in Mice," Molecular Cell, 2008, vol. 31 (6), pp. 785-799.
Behlke M.A., "Chemical Modification of siRNAs for in Vivo Use," Oligonucleotides, 2008, vol. 18 (4), pp. 305-319.
Bell A.J., et al., "An Information-Maximization Approach to Blind Separation and Blind Deconvolution," Neural Computation, 1995, vol. 7 (6), pp. 1129-1159.
Carmell M.A., et al., "MIWI2 is Essential for Spermatogenesis and Repression of Transposons in the Mouse Male Germline," Developmental Cell, 2007, vol. 12 (4), pp. 503-514.
Chen X., et al., "Chemical Modification of Gene Silencing Oligonucleotides for Drug Discovery and Development," Drug Discovery Today, 2005, vol. 10 (8), pp. 587-593.
Corey D.R., "Chemical Modification: The Key to Clinical Application of RNA Interference?," Journal of Clinical Investigation, 2007, vol. 117 (12), pp. 3615-3622.
Crooke S.T., et al., "Kinetic Characteristics of *Escherichia coli* RNase H1: Cleavage of Various Antisense Oligonucleotide-RNA Duplexes," Biochemical Journal, 1995, vol. 312 (Pt 2), pp. 599-608.
Crooke S.T., "Molecular Mechanisms of Antisense Drugs: RNase H," Antisense and Nucleic Acid Drug Development, 1998, vol. 8 (2), pp. 133-134.
Crooke S.T., "New Drugs and Changing Disease Paradigms," Nature Biotechnology, 1996, vol. 14 (3), pp. 238-241.
Crooke S.T., "Progress in Antisense Technology: The End of the Beginning," Methods in Enzymology, 2000, vol. 313 (Antisense Technology, Part A), pp. 3-45.
Day J.J., et al., "Cognitive Neuroepigenetics: A Role for Epigenetic Mechanisms in Learning and Memory," Neurobiology of Learning and Memory, 2011, vol. 96 (1), pp. 2-12.
Day J.J., et al., "Epigenetic Mechanisms in Cognition," Neuron, 2011, vol. 70 (5), pp. 813-829.
De Fazio S., et al., "The Endonuclease Activity of Mili Fuels piRNA Amplification that Silences LINE1 Elements," Nature, 2011, vol. 480 (7376), pp. 259-263.
Dickinson P.J., et al., "Canine Spontaneous Glioma: A Translational Model System for Convection-Enhanced Delivery," Neuro-Oncology, 2010, vol. 12 (9), pp. 928-940.
Feng J., et al., "Dnmt1 and Dnmt3a Maintain DNA Methylation and Regulate Synaptic Function in Adult Forebrain Neurons," Nature Neuroscience, 2010, vol. 13 (4), pp. 423-430.
Huang Da W., et al., "Systematic and Integrative Analysis of Large Gene Lists Using DAVID Bioinformatics Resources," Nature Protocols, 2009, vol. 4 (1), pp. 44-57.
International Search Report and Written Opinion for Application No. PCT/US2014/028196, mailed on Jul. 15, 2014, 15 pages.

(Continued)

*Primary Examiner* — Jane Zara
(74) *Attorney, Agent, or Firm* — David A. Casimir; Casimir Jones, S.C.

(57) ABSTRACT

Provided herein are compositions and methods for the alteration of neuronal methylation by synthetic piRNAs or by alteration of piRNA function. Such alterations find use in the regulation and control of neural gene expression and concomitant neural functions. Further provided herein are systems and methods for the identification of target sites for regulation by piRNAs.

12 Claims, 3 Drawing Sheets

(56) References Cited

OTHER PUBLICATIONS

Kuramochi-Miyagawa S., et al., "DNA Methylation of Retrotransposon Genes is regulated by Piwi Family Members MILI and MIWI2 in Murine Fetal Testes," Genes & Development, 2008, vol. 22 (7), pp. 908-917.

Langmead B., et al., "Ultrafast and Memory-Efficient Alignment of Short DNA Sequences to the Human Genome," Genome Biology, 2009, vol. 10 (3), pp. R25.

Lister R., et al., "Finding the Fifth Base: Genome-Wide Sequencing of Cytosine Methylation," Genome Research, 2009, vol. 19 (6), pp. 959-966.

Lister R., et al., "Human DNA Methylomes at Base Resolution Show Widespread Epigenomic Differences," Nature, 2009, vol. 462 (7271), pp. 315-322.

Roth T.L., et al., "Epigenetic Modification of Hippocampal Bdnf DNA in Adult Rats in an Animal Model of Post-Traumatic Stress Disorder," Journal of Psychiatric Research, 2011, vol. 45 (7), pp. 919-926.

Sah D.W., et al., "Oligonucleotide Therapeutic Approaches for Huntington Disease," Journal of Clinical Investigation, 2011, vol. 121 (2), pp. 500-507.

Siomi M.C., et al., "PIWI-Interacting Small RNAs: the Vanguard of Genome Defence," Nature Reviews Molecular Cell Biology, 2011, vol. 12 (4), pp. 246-258.

Trapnell C., et al., "Transcript Assembly and Quantification by RNA-Seq Reveals Unannotated Transcripts and Isoform Switching During Cell Differentiation," Nature Biotechnology, 2010, vol. 28 (5), pp. 511-515.

Veiseh O., et al., "Cancer Cell Invasion: Treatment and Monitoring Opportunities in Nanomedicine," Advanced Drug Delivery Reviews, 2011, vol. 63 (8), pp. 582-596.

Zheng D., et al., "Topical Delivery of siRNA-Based Spherical Nucleic Acid Nanoparticle Conjugates for Gene Regulation," Proceedings of the National Academy of Sciences, 2012, vol. 109 (30), pp. 11975-11980.

\* cited by examiner

ALTERATION OF NEURONAL GENE EXPRESSION BY SYNTHETIC PIRNAS AND BY ALTERATION OF PIRNA FUNCTION

The present application claims priority to U.S. Provisional Application Ser. No. 61/784,353, filed Mar. 14, 2013, which is herein incorporated by reference in its entirety.

This invention was made with government support under Contract No. FA8650-13-C-7340 awarded by the Department of the Air Force. The government has certain rights in the invention.

FIELD

Provided herein are compositions and methods for the alteration of neuronal methylation by synthetic piRNAs or by alteration of piRNA function. Such alterations find use in the regulation and control of neural gene expression and concomitant neural functions. Further provided herein are systems and methods for the identification of target sites for regulation by piRNAs.

BACKGROUND

Neurological functions and pathologies and resulting properties and phenotypes (e.g., behavior, memory, disease, etc.) are fundamentally important aspects of animal (e.g., human) biology, health, and well-being. Yet the underlying molecular and cellular biology is poorly understood. In view of this, there is a dearth of pharmaceutical or research tools for altering these properties and phenotypes at the molecular level and in a specific manner.

SUMMARY

Provided herein are compositions and methods for the alteration of neuronal methylation by synthetic piRNAs or by alteration of piRNA function. Such alterations find use in the regulation and control of neural gene expression and concomitant neural functions. Further provided herein are systems and methods for the identification of target sites for regulation by piRNAs.

For example, in some embodiments, provided herein are methods for identifying neural piRNA targets (sequences that are regulated, e.g., have altered methylation, by endogenous or synthetic piRNAs), comprising identifying differentially methylated gene-expression regulatory sequences in neural tissue between a control subject and a test subject. Any difference can be identified, including, but not limited to differences associated with a memory task (where the test subject and control subject differ in the performance of a memory task), behavior task, neurological disease or condition, drug administration, therapy administration (e.g., meditation, etc.).

Further provided are synthetic piRNA molecules comprising a chemical modification that improves one or more or all of nuclease stability, decreased likelihood of triggering an innate immune response, lowering incidence of off-target effects, and improved pharmacodynamics relative to a non-modified piRNA. In some embodiments, the piRNA has a nucleotide with at least one chemical modification selected from: phosphorothioate, boranophosphate, 4'-thio-ribose, locked nucleic acid, 2'-O-(2'-methoxyethyl), 2'-O-methyl, 2'-fluoro, 2'-deoxy-2'-fluoro-b-D-arabinonucleic acid, Morpholino nucleic acid analog, and Peptide nucleic acid analog. In some embodiments, the piRNA is attached to a nanoparticle configured to cross the blood-brain barrier.

Also provided herein are molecules useful in the regulation of endogenous or non-endogenous piRNA regulated neural pathways. For example, in some embodiments, provided herein are antisense oligonucleotides having a sequence complementary to an endogenous piRNA found in neural tissue. In some embodiments, synthetic piRNAs are provided that alter methylation of an endogenous neural nucleic acid not known to be regulated by an endogenous piRNA. Thus, in some embodiments, provided herein are methods for altering neural gene expression comprising: administering a synthetic piRNA to a subject under conditions such that methylation of a regulatory sequence regulating the gene is altered.

Further provided herein are neural cells or tissue comprising a synthetic piRNA, a synthetic inhibitor of an endogenous piRNA (e.g., an antisense oligonucleotide specific for the piRNA).

DEFINITIONS

Figure 1:
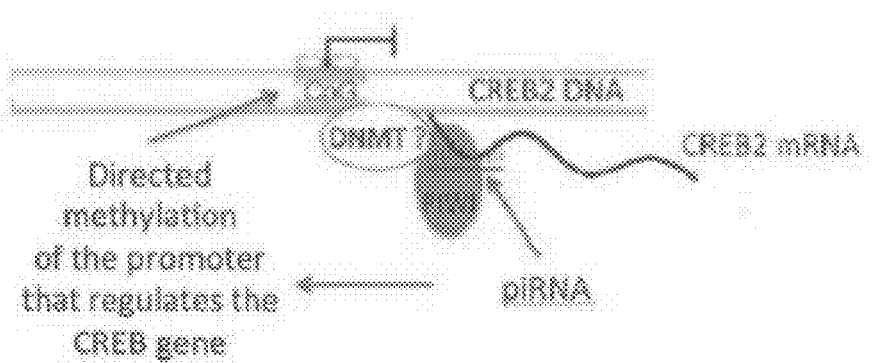
FIG. 1 shows a graphical representation of control of the CREB gene by a piRNA. The piRNA binds to the PIWI proteins and a DNA methyl transferase and mediates methylation of a CpG motif that silences further expression of the CREB gene (15).

The terms "sample" and "specimen" are used in their broadest sense and encompass samples or specimens obtained from any source. As used herein, the term "sample" is used to refer to biological samples obtained from animals (including humans), and encompasses fluids, solids, tissues, and gases. In some embodiments of this invention, biological samples include neural tissue or cells, cerebrospinal fluid (CSF), serous fluid, urine, saliva, blood, and blood products such as plasma, serum and the like. However, these examples are not to be construed as limiting the types of samples that find use with the present invention.

As used herein, the terms "host," "subject" and "patient" refer to any animal, including but not limited to, human and non-human animals (e.g., dogs, cats, cows, horses, sheep, poultry, fish, crustaceans, etc.) that is studied, analyzed, tested, diagnosed or treated. As used herein, the terms "host," "subject" and "patient" are used interchangeably, unless indicated otherwise.

As used herein, the term "effective amount" refers to the amount of a composition (e.g., a synthetic piRNA) sufficient to effect beneficial or desired results. An effective amount can be administered in one or more administrations, applications or dosages and is not intended to be limited to a particular formulation or administration route.

As used herein, the terms "administration" and "administering" refer to the act of giving a drug, prodrug, or other agent, or therapeutic treatment (e.g., compositions of the present invention) to a subject (e.g., a subject or in vivo, in vitro, or ex vivo cells, tissues, and organs). Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) (e.g., multiple synthetic piRNAs or a piRNA or anti-piRNA molecule and another therapeutic) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "treatment" or grammatical equivalents encompasses the improvement and/or reversal of the symptoms of disease (e.g., neurodegenerative disease) or condition. A compound which causes an improvement in any parameter associated with disease when used in the screening methods of the instant invention may thereby be identified as a therapeutic compound. The term "treatment" refers to both therapeutic treatment and prophylactic or preventative measures. For example, those who may benefit from treatment with compositions and methods of the present invention include those already with a disease and/or disorder (e.g., neurodegenerative disease) as well as those in which a disease and/or disorder is to be prevented (e.g., using a prophylactic treatment).

As used herein, the term "at risk for disease" refers to a subject (e.g., a human) that is predisposed to experiencing a particular disease. This predisposition may be genetic (e.g., a particular genetic tendency to experience the disease, such as heritable disorders), or due to other factors (e.g., age, weight, environmental conditions, exposures to detrimental compounds present in the environment, etc.). Thus, it is not intended that the present invention be limited to any particular risk, nor is it intended that the present invention be limited to any particular disease.

As used herein, the term "suffering from disease" refers to a subject (e.g., a human) that is experiencing a particular disease. It is not intended that the present invention be limited to any particular signs or symptoms, nor disease. Thus, it is intended that the present invention encompass subjects that are experiencing any range of disease (e.g., from sub-clinical manifestation to full-blown disease) wherein the subject exhibits at least some of the indicia (e.g., signs and symptoms) associated with the particular disease.

As used herein, the terms "disease" and "pathological condition" are used interchangeably to describe a state, signs, and/or symptoms that are associated with any impairment of the normal state of a living animal or of any of its organs or tissues that interrupts or modifies the performance of normal functions, and may be a response to environmental factors (such as malnutrition, industrial hazards, or climate), to specific infective agents (such as worms, bacteria, or viruses), to inherent defect of the organism (such as various genetic anomalies, or to combinations of these and other factors).

The term "compound" refers to any chemical entity, pharmaceutical, drug, and the like that can be used to treat or prevent a disease, illness, sickness, or disorder of bodily function.

Compounds comprise both known and potential therapeutic compounds. A compound can be determined to be therapeutic by screening using screening methods. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of disease (e.g., neurodegenerative disease).

As used herein, the term "pharmaceutical composition" refers to the combination of an active agent (e.g., a piRNA) with a carrier, inert or active, making the composition especially suitable for diagnostic or therapeutic use in vitro, in vivo or ex vivo.

As used herein, the term "nucleic acid molecule" refers to any nucleic acid containing molecule, including but not limited to, DNA or RNA (e.g., piRNA). The term encompasses sequences that include any of the known base analogs of DNA and RNA including, but not limited to, 4-acetylcytosine, 8-hydroxy-N-6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil,5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxy-aminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the terms "gene expression" and "expression" refer to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refer to regulation that increases and/or enhances the production of gene expression products (e.g., RNA or protein), while "down-regulation" or "repression" refer to regulation that decrease production. Molecules (e.g., transcription factors) that are involved in up-regulation or down-regulation are often called "activators" and "repressors," respectively.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form.

The term "synthetic" when used in reference to nucleic acid molecules (e.g., piRNA) refers to non-natural molecules made directly (e.g., in a laboratory) or indirectly (e.g., from expression in a cell of a construct made in a laboratory) by mankind.

DETAILED DESCRIPTION

Provided herein are compositions and methods for the alteration of neuronal methylation by synthetic piRNAs or by alteration of piRNA function. Such alterations find use in the regulation and control of neural gene expression and concomitant neural functions. Further provided herein are systems and methods for the identification of target sites for regulation by piRNAs.

Epigenetic molecular mechanisms, specifically histone post-translational modifications and cytosine methylation of DNA, have recently been discovered to be critically important regulators of learning and memory (1). Provided herein are compositions and methods related to identifying and understanding that association of methylation with learning and memory, as well as other neurological functions, properties, and health status. Further provided herein are drug treatments to augment learning and enhance memory formation and stabilization. Such enhancement and stabilization has many uses, including, but not limited to accelerated training of individuals (e.g., athletes, professionals, and military personnel) and treatment of diseases and disorders of the brain and central nervous system (e.g., traumatic brain injury, psychiatric, cognitive diseases, neurodegenerative disease, post-traumatic stress disorder (PTSD), etc.).

Conventional approaches to target identification and validation have evolved steadily over decades and have benefited by the availability of newer observational tools such as microarrays and interventional tools such as antisense and RNA interference. However, recent breakthroughs is epigenomic science have provided a far superior approach based on whole methylome sequencing (2). It is now possible to construct a relevant animal model (e.g., mouse) for a neural process, such as consolidation of memory, identify and separate the important cell types (e.g. pyramidal neurons of the hippocampus), and sequence the complete methylome of these cells from untrained and memory trained subjects and identify methylation changes associated with every gene in the target cell type. This powerful approach avoids the "looking under the lamppost" bias of previous target identification strategies. In addition to sequencing the methylome, the expressed RNA from these cells can also be sequenced to provide a broad picture of the impact of methylation changes on gene expression. Identification of the methylation changes in the DNA and expressed RNA provide direct evidence of what genes are needed for the process being studied and therefore what genes to turn off to block the process by a pharmacological intervention. Provided herein are synthetic piRNA molecules that alter methylation in a specific and directed manner, providing systematic control over gene expression. Also provided herein are molecules that regulate endogenous piRNA function.

Oligonucleotide drugs work by a variety of mechanisms, the simplest of which is simply hybridizing to the target mRNA and blocking its natural ability to direct protein synthesis by steric hindrance (3, 4). However, it was realized early on that the potency of oligonucleotide drugs can be substantially enhanced by co-opting a natural pathway such as activating endogenous enzymes such as RNAse H, resulting destruction of the target RNA through enzymatic cleavage (5, 6). As the understanding of the various roles of RNA in the cell grew, opportunities became available to exploit these newly discovered pathways. The discovery of the siRNA pathway in the 1990's led to opportunity to create double stranded RNA mimetics of natural siRNA's to silence genes (7-9). However, a common feature of all therapeutic uses of oligonucleotides is that the biological effects brought about by the drug are transient and require a sustained presence of the drug to maintain the desired pharmacological effect. This is a problem for treating the brain, where delivery of the drug to the target cells is much more challenging than other target tissues. Successful treatment of the brain requires stable and potent oligonucleotides capable of surviving the journey to the brain but more importantly, the oligonucleotides should produce a sustained biological effect in the brain that persists after the oligonucleotide drug is gone.

Technology provided herein achieves this result by co-opting the piRNA pathway to directly impact the silencing or activating the target genes in the brain through directed changes in DNA methylation. These changes in DNA methylation can be long acting and even permanent for the life of the cell if not actively reversed.

piRNAs are a distinct set of small non-coding RNA in the typical size range of 26-32 or 33 nucleotides (ranges from 19-33 have been reported), typically with a U on the 5'-end and a 2'-OMethyl modified 3'-end. The first role discovered for the piRNA pathway is the protection of the integrity of germ line cells from parasitic invasion of transposable element DNA (10). Transposable elements are endogenous genomic parasites that threaten the integrity of the host genome by jumping to new locations in the host DNA and possibly landing in regions that might disrupt the function of normal genes. The cellular countermeasure to protect the genome from disruption is, by necessity, powerful and long-lasting, and is accomplished through silencing of the transposable elements by both directing cleavage of the transposable element RNA and by directing DNA methylation to permanently silence the transposable element. piRNA accomplishes this binding in an antisense fashion to the target gene mRNA and, through interactions with a specific set of proteins (the Piwi protein complex), trigger both the destruction of the mRNA and methylation of the DNA that controls silencing of the target gene (11, 12). This latter effect is the key to producing a sustained biological response.

The piRNA pathway has been recently been studied most for its role in protection of the germ-line DNA (10, 13). It is now known that the piRNA pathway is broadly conserved in evolution and has a broad role in various tissues including the mammalian central nervous system in the hippocampal neurons, extending into the dendritic compartment of the cell (14). Most intriguing is a very recent report from the Kandel laboratory that neuronal piRNA's play a role in epigenetic control of memory-related synaptic plasticity in *Aplysia*. They discovered the presence of abundantly expressed piRNA in the brain and that piRNA directs serotonin-dependent methylation and silencing of the CREB2 gene, a major inhibitory constraint of memory, leading to long term synaptic facilitation (15).

This observation is consistent with a growing body of recent evidence from the laboratory of Sweatt and colleagues who have shown that DNA methylation is involved in multiple aspects of memory formation and maintenance (1, 16-21). Epigenetic changes in cellular differentiation are generally permanent, but not in adult neurons, where the plastic nature of synaptic neurons requires long-term but reversible changes in gene expression.

In some embodiments, provided herein are target identification systems and methods for identifying fundamental mechanisms underlying memory formation at the whole genome level and for identifying targets for therapeutic intervention. Further provided are therapeutic and research agents for altering methylation, and thus gene expression, at these target sequences so as to regulate neurological functions (e.g., memory, learning, etc.) and pathologies.

The piRNA pathway provides a molecular targeting mechanism to link to the epigenetic changes associated with memory. Multiple mechanisms of intervention are provided including: 1) antisense oligonucleotide targeting of specific endogenous piRNA's and interfering with their function to mediate gene silencing, producing long term gene expression that would otherwise be silenced, and 2) piRNA mimetic drugs (e.g., synthetic piRNAs) that specifically silence target genes. It is important to note that the latter mechanism does not specifically require that the gene (to be silenced) be naturally regulated by a piRNA, but can be any gene. All that is required is that the target cell contains an active piRNA pathway for any purpose that is co-opted for therapeutic intervention. The existence of this pathway in neurons (14, 15) allows this strategy.

In some embodiments, provided herein are synthetic piRNA molecules. In some embodiments, the piRNA molecules comprise chemical modification to improve nuclease stability, decrease the likelihood of triggering an innate immune response, lower the incidence of off-target effects, and/or improve pharmacodynamics relative to non-modified molecules so as to increase potency and specificity. In some embodiments, the molecules are loaded onto nanoparticles, providing a stabilizing effect (e.g., protecting against nuclease degradation). These effects are particularly important for nucleic acids intended to treat the brain, where the delivery challenges limit the amount of active nucleic acid drug that will reach the target cells. Therefore, nucleic acid drugs used to treat the brain should be based on chemistry with high potency and a long duration of action. Similarly, the pharmacological targets of the molecules should have high leverage to create a sustained biological response. Exemplary chemical modifications of nucleotides (e.g., modifications of the sugars) in the synthetic piRNA molecules that find use in some embodiments of the technology include the following: phosphorothioate, boranophosphate, 4'-thio-ribose, locked nucleic acid, 2'-O-(2'-methoxyethyl), 2'-O-methyl, 2'-fluoro, 2'-deoxy-2'-fluoro-b-D-arabinonucleic acid, Morpholino nucleic acid analog, and Peptide nucleic acid analog. Additional modification used with antisense oligonucleotides may be employed (see e.g., US Pat. Publ. Nos. 2012/0202874 and 2012/0149755, herein incorporated by reference in their entireties).

In some embodiments, antisense oligonulceotides that interact with and interfere with endogenous piRNA sequences are used.

Delivery of synthetic piRNA molecules or antisense oligonucleotides may be accomplished by any desired method. In some embodiments, molecules are delivered intrathecally. In some embodiments, a Medtronic infusion system employing an implantable, battery-powered drug-infusion pump is used to deliver molecules to the striatum (Dickinson et al., Neuro. Oncol. 12:928-940 (2010); Sah and Aronin, J. Clin. Invest. 121: 500-507 (2011)). In some embodiments, intranasal delivery is used. In some embodiments, nucleic acids are delivered by nanoparticles. For example, particles comprising an iron-oxide core coated with chitsan may be used (see e.g., Veiseh et al., Adv. Drug Deliv. Rev., 8:582 (2011)). Chitosan is a transcytosing molecule that is able to cross the blood brain barrier. In some embodiments, the particles are associated with a call-penetrating peptide to facilitate delivery of the nucleic into cells. In some embodiments, endogenous nanoparticles (e.g., high-density lipoproteins) are used to deliver molecules across the blood brain barrier.

EXAMPLE 1

Target Identification

This example describes methods for identifying targets for piRNA regulation, for example, associated with loci where target sequences are not currently known.

Epigenetic Mouse Model Experiments.

The approach encompasses two key experiments, using laboratory animals in molecular, genetic, epigenetic, and behavioral studies. For both assays, one uses genetically engineered mice that have a specific neuronal subpopulation (pyramidal neurons) labeled in the hippocampus, and couple the use of these mice with FACS in order to isolate a uniquely defined sample of cells for epigenetic characterization.

In some embodiments, one can selectively manipulate DNA methylation in the mouse CNS in vivo, using IntraCerebroVentricular (ICV) infusion of a DNA MethylTransferase inhibitor (DNMTi). High-throughput DNA sequencing and subsequent epigenomic bio-informatic analysis identifies target sites associated with particular phenotypic changes providing targets for manipulation by piRNA regulation.

A second series of experiments utilizes spatial, hippocampus-dependent learning and memory in the behaving animal as a stimulus, in order to trigger learning-related epigenetic (DNA methylation) changes in the hippocampus. Using hippocampal pyramidal neurons isolated from control and trained animals, subsequent use of methylomic analysis defines memory associated DNA methylation changes for the entire cellular epigenenome with specificity at the single-nucleotide level.

These assays identify target genes whose methylation is changed and whose transcription is blocked or increased by DNMT inhibition. These assays thus correlate a function memory change (memory blockade) with a specific set of epigenetic alterations (DNA methylation) and a specific set of transcriptional changes (mRNA and small non-coding RNA readout).

One can further identify at single-nucleotide resolution the complete set of genes whose epigenetic cytosine methylation changes in response to hippocampus dependent spatial learning, and correlate this to the list of genes whose transcription is regulated with memory formation. These assays can define the specific cellular locus for the changes in the methylome by utilizing gene engineering-based fluorescent tagging to specifically isolate hippocampal pyramidal neurons, a neuronal sub-population known to be involved in spatial learning and memory.

The Jackson Lab has commercially available a mouse line (Stock Number 003782) that selectively labels CNS neurons using Yellow Fluorescent Protein (YFP) (2). This model is well suited for the above assays. These mice are beneficial because the genome databases are well developed for this species, making the methylomics efficient. Further, this engineered mouse line has specifically labeled neurons that are advantageous, because one can use FACS to isolate specific neurons (hippocampal pyramidal neurons) that are known to be involved in and necessary for spatial learning and memory.

This approach is illustrated below for the assessment of fear response. The mouse model is used for behavioral modeling of learning, short-term memory, and long-term memory—specifically contextual fear conditioning. After training animals in this learning and memory paradigm, bioinformatics and high-throughput nucleotide sequencing approaches are used to comprehensively identify memory-associated changes in the methylome.

Interventive experiment to manipulate the epigenome are also conducted, using a class of agents that are known to affect memory capacity: DNMT inhibitors. Animals (control cannulated versus drug-infused) are treated with this agent and epigenomic and transcriptomic changes are assessed using the methylomics approaches described above.

Mice are trained and evaluated using a behavioral test and associated control paradigms that assess baseline behaviors, sensory responses, and hippocampus-dependent memory formation. The Conditioned Fear Paradigm utilizes automated conditioned fear chambers. The automated test chambers use a video detection system and are placed into sound-attenuated chambers. The conditioned fear test is routinely used to study fear/emotional-based learning and memory in rodents, and has quickly become one of the most widely used assays for learning and memory performance in mutant mice. For these experiments, an aversive stimulus (in this case, a mild foot shock) is paired either once or 3 times with an auditory conditioned stimulus (CS, white noise) within a novel environment. When tested 24 h after training, mice exhibit marked fear, measured by freezing behavior, in response to re-presentation of either the context (contextual fear conditioning) or the auditory CS delivered in a different context (cued fear conditioning). One also evaluates contextual fear conditioning by itself without presenting the auditory cue during training in the novel context. Cued fear conditioning is thought to be dependent upon the amygdala, whereas contextual fear conditioning also likely involves the hippocampus. To assess baseline behavior, one monitors animals during the training phase. One assesses both baseline freezing behavior prior to presentation of the foot shock on the training day (minutes 1-3), and the freezing of the animal in response to foot shock. Freezing on the training day in response to application of the foot shock is also used as a crude estimate of shock sensitivity.

For the fear conditioning experiments mice are transported to the laboratory at least 30 min prior to fear conditioning. Fear conditioned animals are allowed to explore the training chamber for 2 min, after which they receive a series of three electric shocks (1 s, 0.5 mA) at 2 min intervals. As controls, context exposed (context only) or latent inhibition plus fear conditioned (latent inhibition) animals are also placed in the novel training chambers. Context only animals are placed in the novel training chamber for 7 min without receiving the footshock.

Latent Inhibition animals are pre-exposed to the context for 2 h before the same 7 min training protocol is administered as described for the fear conditioned animals. In all shocked groups the animals are allowed to explore the novel context (training chamber) for an additional 1 min after the receiving the final footshock prior to being returned to their home cage. Footshock alone control animals are taken to the training room, placed in the training chamber and immediately shocked and removed from the chamber. Freezing behavior is recorded using Video Freeze software (Med Associates, St. Albans, Vt.). Another group of age-matched animals that are handled by the experimenter but do not receive any experimental manipulations are used as naive controls in these experiments as well.

Cannula Implantation and Intra-CNS Infusion of DNMTi-In Vivo CNS-selective inhibition of DNMTs uses cannula-based direct infusion of agents into the cerebral ventricles. For DNMT inhibition, the cytosine analogs zebularine and 5-aza-2-deoxycitidine (in separate experiments) are used, which selectively inhibit all known DNMTs (i.e., DNMT1, 3A, and 3B). For stereotaxic surgery, mice are anesthetized with ketamine and xylazine and secured in a Kopf stereotaxic apparatus. Bilateral stainless steel guide cannulae (26G; Plastics One, Roankoke, Va.) are aimed at the ventricles. Clearance through the guide cannulae is maintained with 33G obdurators (Plastics One) cut to project 1 mm (Area CA1) or 0.2 mm (ACC) beyond the tip of the guide. Animals are habituated to dummy cannula removal and given 5 days of recovery and handling before the start of behavioral conditioning, etc. To ensure accurate cannula placement, brains are collected from those animals given both fear conditioning training and a retention test. Sections are collected and stained with cresyl violet to verify the location of the infusion needle tips.

Statistical analyses are conducted using the PC software program Prism. Two-sample comparisons are made using the paired Student's t test, and multiple comparisons are made using a one-way analysis of variance (ANOVA), Tukey test, or the Fisher PLSD test. All behavioral experiments are assessed using analysis of variance (ANOVA)

followed by post-hoc analysis with the Tukey-Kramer test where appropriate. If data sets do not meet the criteria required for parametric statistical analysis, then a Kruskal-Wallis ANOVA is performed, followed by a post-hoc Dunn's multiple comparison test.

Methylome and RNA Sequencing

MethylC-Seq library generation: 1-5 µg of genomic DNA is extracted from frozen tissue using the DNeasy Mini Kit (Qiagen) and spiked with 25 ng unmethylated cI857 Sam7 Lambda DNA (Promega). The DNA is fragmented with a Covaris S2 (Covaris) to 100-150 bp, followed by end repair and addition of a 3' A base. Cytosine methylated adapters provided by Illumina (Illumina) are ligated to the sonicated DNA at 16° C. for 16 hours with T4 DNA ligase (New England Biolabs). Adapter-ligated DNA are isolated by two rounds of purification with AMPure XP beads (Beckman Coulter Genomics). Adapter-ligated DNA (S450 ng) are subjected to sodium bisulfite conversion using the Methyl-Code kit (Life Technologies) as per manufacturer's instructions. The bisulfite-converted, adapter-ligated DNA molecules are enriched by 4 cycles of PCR. The reaction products are purified using AMPure XP beads (two rounds). Up to three separate PCR reactions are performed on subsets of the adapter-ligated, bisulfite-converted DNA, yielding up to three independent libraries from the same biological sample (Please see (23) for detailed protocol). One obtains the final sequence coverage by sequencing all libraries for a sample separately, thus reducing the incidence of "clonal" reads which share the same alignment position and likely originate from the same template molecule in each PCR. The sodium bisulfrte non-conversion rate for each sample is empirically determined by calculation of the frequency of cytosines sequenced at cytosine reference positions in the Lambda genome. Sequencing is performed using the Illumina HiSeq2000 Sequencing System as per the manufacturer's instructions.

Strand-specific mRNA-seq libraries: Samples are processed as described (23). Briefly, total RNA is isolated from tissue or FACS isolated cells by treatment with RNA later and using the mirVana miRNA isolation kit and treated with DNaseI (Qiagen) for 30 min at room temperature. Following ethanol precipitation, biotinylated LNA oligonucleotide rRNA probes complementary to the 5S, 5.8S, 12S, 18S and 28S ribosomal RNAs are used to deplete rRNA from 20 µg of total RNA in two sequential RiboMinus reactions (Life Technologies) as per manufacturer's instructions.

Unique 5' and 3' RNA oligonucleotides are then sequentially ligated to the ends of fragments of RNA devoid of rRNA. Sequencing is performed using the Illumina HiSeq2000 Sequencing System as per the manufacturer's instructions.

smRNA-Seq library generation: RNA fractions enriched for small RNAs are isolated from tissue or FACS isolated cells by treatment with RNAlater (Life Technologies) and using the mirVana miRNA isolation kit (Life Technologies) and treated with DNaseI (Qiagen) for 30 min at room temperature. Following ethanol precipitation, small RNAs are separated by electrophoresis on a 15% TBE-urea gel and RNA molecules between approximately 10 and 50 nt are then excised and eluted from the gel fragments. Following ethanol precipitation, smRNA-Seq libraries are produced using the Small RNA Sample Prep v1.5 kit (Iliumina) as per manufacturer's instructions. Sequencing is performed using the Iliumina HiSeq2000 Sequencing System as per the manufacturer's instructions.

Data Analysis

MethylC-seq data is mapped and processed as described in Lister et al (23). Briefly, reads are first be trimmed of any adapter sequences at the 3' end, and subsequently mapped to the NCBI m37 reference genome with Bowtie (24), using the following parameters: -e 90-I 20-n O-k 10-nomaground-solexa1.3-quals. Mapped reads are filtered as follows: any read with more than 3 mismatches is trimmed from the 3' end to contain 3 mismatches, and any read pair which contained a cytosine mapped to a reference sequence thymine is removed. Reads are then collapsed to remove clonal reads potentially produced in the PCR amplification from the same template molecule, based on common start position of read 1. Methylcytosines are identified from the mapped and processed read data as described in (23), including correction of any DNA methylation incorrectly categorized as non-CG due to SNPs in the sample versus reference genomes.

Profiling DNA methylation in promoters and gene bodies. Promoters are defined as within 2 kb upstream regions starting from the transcription start site (TSS) of the Ensembl transcript IDs (NCBI BUILD 37.1). Gene bodies are determined for each Ensembl transcript 10 as the region spanning from the TSS to the end of transcription site. Each promoter and gene body is divided in twenty equally sized bins and the density of CG, and absolute (mCG) and relative (mCG/CG) methylation is determined for each bin. Absolute methylation is computed as the average methylation level (methylated I (methylated+unmethylated) read counts) divided by the bin size in bp. Relative methylation is determined as the ratio between the absolute methylation and the CG density (CG/bp) in the same bin. Similar analyses are performed for any methylation identified in the non-CG context.

Mapping of mRNA-Seq data: RNA-Seq read sequences produced by the Illumina analysis pipeline is aligned with the CLCbio to the NCBI Build 37.1 C57BU6 mouse reference sequence. Reads that align to multiple positions are discarded. Reads per kilobase of transcript per million reads (RPKM) values are calculated with the Cufflinks software (25) using mouse RefSeq gene models.

Mapping of smRNA.seq reads. smRNA sequence reads in FastQ format are produced by the Illumina analysis pipeline. smRNA-Seq reads that contain at least 5 bases of the 3' adapter sequence are selected and this adapter sequence removed, retaining the trimmed reads that are from 16 to 37 nt in length. These processed reads in FastQ format are then aligned to the mouse reference genome (NCBI BUILD 37.1) with the Bowtie alignment algorithm using the following parameters: -solexa-quals-e1-120-n 0-a-m 1000-best—no-maqround. Consequently, any read that aligns with no mismatches and to no more than 1000 locations in the NCBI BUILD 37.1 reference genome sequence is retained for downstream analysis.

Post-processing data analysis: One performs dimensionality reduction of the MethylC-Seq and RNA-Seq datasets by keeping only those genes showing at least 2-fold methylation or expression changes across the different conditions. The remaining expression values are then log-transformed for Independent Component Analysis (26). ICA is an unsupervised machine-learning algorithm that is used to identify the contribution on methylation states and gene expression of genes that were most strongly affected. The expression value of any gene or methylation state is viewed as a result of several independent sources (components) that contribute to its expression, treatment and disease state being examples. ICA allows separation of these components without prior knowledge. The genes that rank highly on this list are subjected to manual inspection and interpretation. The ICA sources is mapped into functional categories using DAVID (27) to identify significantly enriched gene ontology categories. The categories with most significant P-values provide insights into the biological processes involved in discriminating between different treatments and conditions. Parallel ICA is used to link the ICA analyses of the MethylC-Seq and the RNA-Seq data sets.

Figure 2:
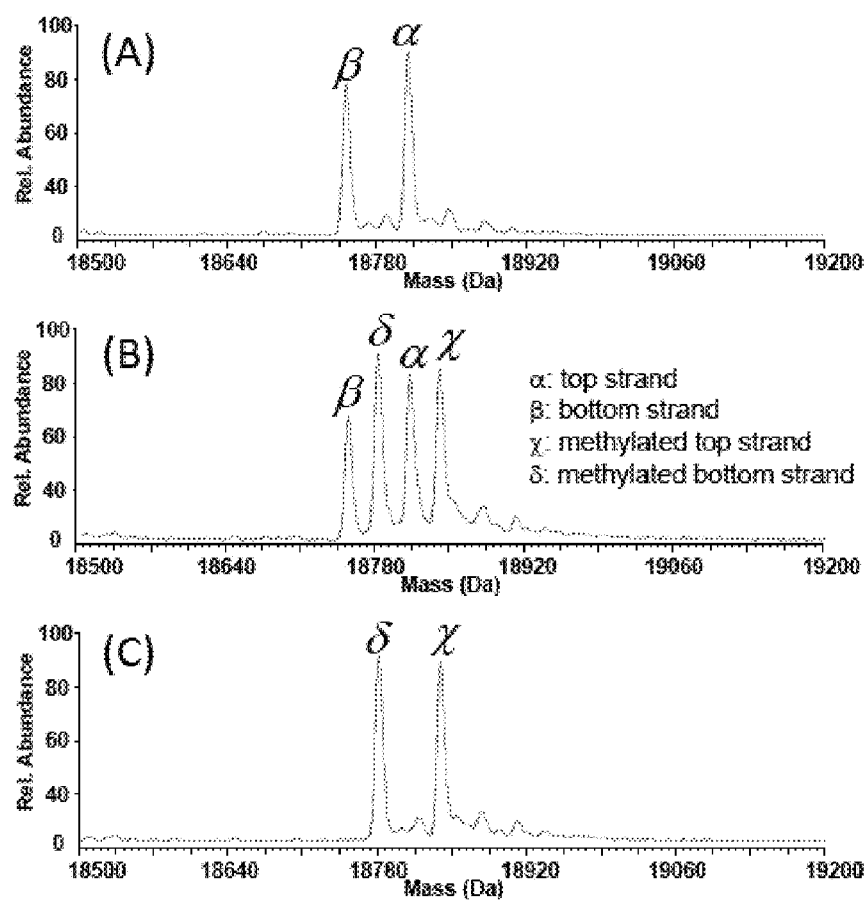
FIG. 2 shows exemplary mass spectral analysis of CREB nucleic acid molecules having different methylation patterns.

In some embodiments, mass spectrometry is used to identify and analyze target methylation sites. FIG. 2 shows data with mass spectra for nucleic acid sequences bracketing a CpG island in a promoter region of the CREB2 gene within the *Aplysia* genome. The detected nucleic acids were generated synthetically as a means to illustrate the capability to detect levels of methylation associated with neuron plasticity. Panel (A) shows both strands of the genomic sequence with no methylation, Panel (B) show the same region with approximately equal amount of unmethylated and methylated cytosines in the CpG island, and Panel (C) illustrates 100% methylation of the CpG island within the promotor sequence. The relative percentage of methylation and non-methylation for the CpG island can be determined by comparison of relative spectral abundances.

| Label | Name | Sequence | Avg. mass (Da) |
|---|---|---|---|
| α | top strand | GCCAAAAAATTGACTAGCGTCTGATTCCACCGCGTTTTGACACTAATTATTGAGTGAAGAG | 18810.18 |
| β | bottom strand | CTCTTCACTCAATAATTAGTGTCAAAACGCGGTGGAATCAGACGCTAGTCAATTTTTTGGC | 18752.13 |
| χ | methylated top strand | GCCAAAAAATTGACTAGCGTCTGATTCCACC5mGC5mGTTTTGACACTAATTATTGAGTGAAGAG | 18838.23 |
| δ | methylated bottom strand | CTCTTCACTCAATAATTAGTGTCAAAAC5mGC5mGGTGGAATCAGACGCTAGTCAATTTTTTGGC | 18780.18 |

Figure 3:
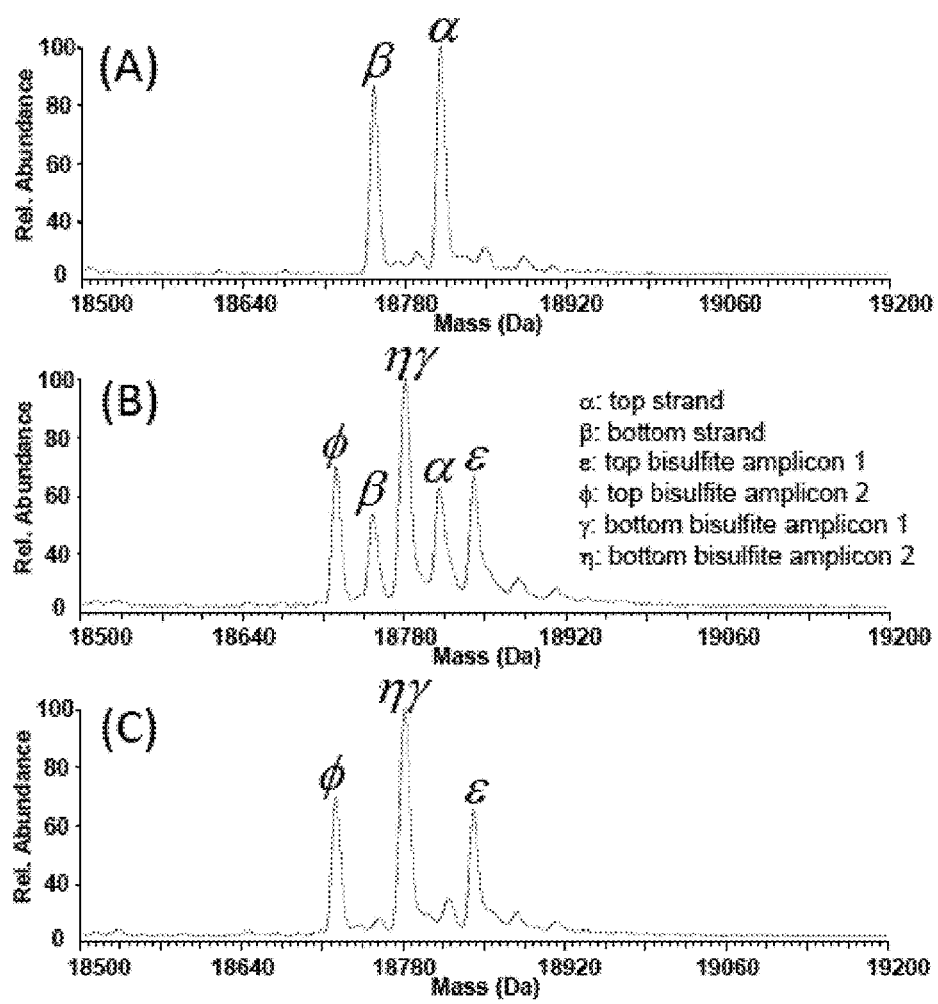
FIG. 3 shows exemplary mass spectral analysis of CREB nucleic acid molecules having different methylation patterns.

FIG. 3 shows mass spectra for nucleic acid sequences bracketing a CpG island in a promoter region of the CREB2 gene within the *Aplysia* genome. The detected nucleic acids were generated synthetically as a means to illustrate the capability to detect levels of methylation associated with neuron plasticity. Panel (A) shows both strands of the genomic sequence with no methylation, Panel (B) show the same region with approximately equal amount of unmethylated and methylated cytosines in the CpG island—the methylated species are represent by nucleic acids identical to amplicons resulting from a bisulfite treatment and PCR amplification process (note that the amplicon products for the bottom strand (g, h) are near mass degenerate, yielding overlapping peaks with essentially linear addition of abundance), and Panel (C) illustrates 100% methylation of the CpG island within the promotor sequence. The relative percentage of methylation and nonmethylation for the CpG island can be determined by comparison of relative spectral abundances.

| Label | Name | Sequence | Avg. mass (Da) |
|---|---|---|---|
| α | top strand | GCCAAAAAATTGACTAGCGTCTGATTCCACCGCGTTTTGACACTAATTATTGAGTGAAGAG | 18810.18 |
| β | bottom strand | CTCTTCACTCAATAATTAGTGTCAAAACGCGGTGGAATCAGACGCTAGTCAATTTTTTGGC | 18752.13 |
| ε | top bisulfite amplicon 1 | GCCAAAAAATTGACTAGCGTCTGATTCCACTGTGTTTTGACACTAATTATTGAGTGAAGAG | 18840.20 |
| φ | top bisulfite amplicon 2 | CTCTTCACTCAATAATTAGTGTCAAAACACAGTGGAATCAGACGCTAGTCAATTTTTTGGC | 18720.13 |
| γ | bottom bisulfite amplicon 1 | CTCTTCACTCAATAATTAGTGTCAAAATGTGGTGGAATCAGACGCTAGTCAATTTTTTGGC | 18782.15 |
| η | bottom bisulfite amplicon 2 | GCCAAAAAATTGACTAGCGTCTGATTCCACCACATTTTGACACTAATTATTGAGTGAAGAG | 18778.18 |

Using the approaches described above, target methylation sites for regulation by piRNA are identified for any desired neural function.

The following references correspond to the number citations above, each of which is herein incorporated by reference in its entirety.

1. Day J J, Sweatt J D. Epigenetic mechanisms in cognition. Neuron 2011; 70(5):813-829.
2. Lister R, Ecker J R. Finding the fifth base: genome-wide sequencing of cytosine methylation. Genome Res 2009; 19(6):959-966.
3. Crooke S T. Progress in antisense technology: the end of the beginning Methods Enzymol 2000; 313(Antisense Technology, Part A):3-45.
4. Crooke S T. New drugs and changing disease paradigms. Nat Biotechnol 1996; 14(3):238241.
5. Crooke S T, Lemonidis K M, Neilson L, et al. Kinetic characteristics of *Escherichia coli* RNase HI: cleavage of various antisense oligonucleotide-RNA duplexes. Biochem J 1995; 312 (Pt 2):599-608.
6. Crooke S T. Molecular mechanisms of antisense drugs: RNase H. Antisense Nucleic Acid Drug Dev 1998; 8(2):133-134.
7. Chen X, Dudgeon N, Shen L, et al. Chemical modification of gene silencing oligonucleotides for drug discovery and development. Drug Discov Today 2005; 10(8):587-593.
8. Behlke M A. Chemical modification of siRNAs for in vivo use. Oligonucleotides 2008; 18(4):305-319.
9. Corey D R. Chemical modification: the key to clinical application of RNA interference? J Clin Invest 2007; 117(12):3615-3622.
10. Siomi M C, Sato K, Pezic D, et al. PIWI-interacting small RNAs: the vanguard of genome defence. Nat Rev Mol Cell Bioi 2011; 12(4):246-258.
11. Aravin A A, Sachidanandam R, Bourc'his D, et al. A piRNA pathway primed by individual transposons is linked to de novo DNA methylation in mice. Mol Cell 2008; 31(6):785-799.
12. Kuramochi-Miyagawa S, Watanabe T, Gotoh K, et al. DNA methylation ofretrotransposon genes is regulated by Piwi family members MIL1 and MIWI2 in murine fetal testes. Genes Dev 2008; 22(7):908-917.
13. Carmell M A, Girard A, van de Kant H J, et al. MIWI2 is essential for spermatogenesis and repression oftransposons in the mouse male gennline. Dev Cell 2007; 12(4):503-514.
14. Lee E J, Banerjee S, Zhou H, et al. Identification ofpiRNAs in the central nervous system. RNA 2011; 17(6):1090-1099.
15. Rajasethupathy P, Antonov I, Sheridan R, et al. A role for neuronal piRNAs in the epigenetic control of memory-related synaptic plasticity. Cell 2012; 149(3):693-707.
16. Miller C A, Gavin C F, White J A, et al. Cortical DNA methylation maintains remote memory. Nat Neurosci 2010; 13(6):664-666.
17. Day J J, Sweatt J D. DNA methylation and memory formation. Nat Neurosci 2010; 13(11):1319-1323.
18. Feng J, Zhou Y, Campbell S L, et al. Dnrntl and Dnmt3a maintain DNA methylation and regulate synaptic function in adult forebrain neurons. Nat Neurosci 2010; 13(4):423-430.
19. Miller C A, Sweatt J D. Covalent modification of DNA regulates memory formation. Neuron 2007; 53(6):857-869.
20. Day J J, Sweatt J D. Cognitive neuroepigenetics: a role for epigenetic mechanisms in learning and memory. Neurobiol Learn Mem 2011; 96(1):2-12.
21. Roth T L, Zoladz P R, Sweatt J D, et al. Epigenetic modification of hippocampal BdnfDNA in adult rats in an animal model of post-traumatic stress disorder. J Psychiatr Res 2011; 45(7):919926.
22. Zheng D, Giljohann D A, Chen D L, et al. Topical delivery of siRNA-based spherical nucleic acid nanoparticle conjugates for gene regulation. Proc Natl Acad Sci USA 2012; 109(30): 1197511980.
23. Lister R, Pelizzola M, Dowen R H, et al. Human DNA methylomes at base resolution show widespread epigenomic differences. Nature 2009; 462(7271):315-322.
24. Langmead B, Trapnell C, Pop M, et al. Ultrafast and memory-efficient alignment of short DNA sequences to the human genome. Genome biology 2009; 10(3):R25.
25. Trapnell C, Williams B A, Pertea G, et al. Transcript assembly and quantification by RNASeq reveals unannotated transcripts and isoform switching during cell differentiation. Nat Bioteclmol2010; 28(5):511-515.
26. Bell A J, Sejnowski T J. An information-maximization approach to blind separation and blind deconvolution. Neural Comput 1995; 7(6):1129-1159.
27. Huang da W, Sherman B T, Lempicki R A. Systematic and integrative analysis of large gene lists using DAVID bioinformatics resources. Nature protocols 2009; 4(1):44-57.

We claim:

1. A method for identifying neural piRNA targets, comprising:
   a) providing a test subject;
   b) implanting an intracerebroventricular catheter in said test subject;
   c) infusing an anti-sense oligonucleotide to said neural piRNA target to said test subject through said intracerebroventricular catheter;
   d) administering behavorial/contextual fear conditioning training to said test subject;
   e) comparing memory consolidation after said infusing in said test subject and a control subject;
   f) comparing small RNA induction after said infusing in said test subject and a control subject;
   g) comparing DNA methylation after said infusing in said test subject and a control subject using methylome sequencing; and
   thereby identifying differentially methylated gene-expression regulatory sequences in neural tissue between said control subject and said test subject.

2. The method of claim 1, wherein said test subject differs from the control subject in the performance of a memory task.

3. The method of claim 1, wherein said test subject differs from the control subject in the performance of a behavioral task.

4. The method of claim 1, wherein said test subject differs from the control subject in the presence of a neurological disease or condition.

5. The method of claim 1, wherein said test subject differs from the control subject in the administration of a drug.

6. The method of claim 1, wherein said test subject differs from the control subject in the application of a therapy.

7. The method of claim 1, further comprising administration of a DNA MethylTransferase inhibitor (DNMTi) through said intracerebroventricular catheter.

8. The method of claim 1, wherein said methylome sequencing comprises sodium bisulfite conversion.

9. The method of claim 1, wherein said methylome sequencing comprises methylome sequencing of promoter and gene body regions.

10. The method of claim 1, further comprising habituation to cannula removal before said administering behavorial/contextual fear conditioning.

11. The method of claim 1, further comprising collecting, sectioning and staining a brain of said test subject.

12. The method of claim 1, further comprising strand-specific mRNA and/or smRNA sequencing.

* * * * *